United States Patent [19]

Gallacher et al.

[11] 4,164,474

[45] Aug. 14, 1979

[54] PROCESS FOR PRODUCING METAL SALTS OF OIL-SOLUBLE ORGANOSULFONIC ACIDS

[75] Inventors: Lawrence V. Gallacher, East Norwalk; Robert G. King, West Redding, both of Conn.

[73] Assignee: King Industries, Inc., Norwalk, Conn.

[21] Appl. No.: 736,165

[22] Filed: Oct. 27, 1976

Related U.S. Application Data

[63] Continuation-in-part of Ser. No. 539,595, Jan. 8, 1975, abandoned.

[51] Int. Cl.² .................. C10M 1/40; C10L 1/24; C07C 143/24; C07C 143/02
[52] U.S. Cl. .................................. 252/33; 44/76; 252/389 R; 260/505 C; 260/505 N; 260/513 R
[58] Field of Search ........................... 252/33, 389 R; 260/505 N, 513 R; 44/76

[56] References Cited

U.S. PATENT DOCUMENTS

| 2,514,733 | 7/1950 | Vold et al. ........................ 252/33 |
| 2,688,035 | 8/1954 | Jacob et al. .................. 260/505 N |
| 2,702,280 | 2/1955 | Mackinnon .................. 260/505 N |
| 2,760,970 | 8/1956 | LeSuer ............................... 252/33 |
| 2,764,548 | 9/1956 | King et al. ........................ 252/33 |
| 2,846,466 | 8/1958 | Crosby et al. ................... 252/33 |

*Primary Examiner*—Irving Vaughn
*Attorney, Agent, or Firm*—Morgan, Finnegan, Pine, Foley & Lee

[57] ABSTRACT

An improved process for producing metal salts of organosulfonic acids comprises reacting the sulfonic acid with a slight excess of the corresponding metal carbonate until the carbonate/acid equilibrium point is reached, i.e., the pH of a substantially carbonate- and bicarbonate-free sample stabilizes in the range of 6.0 to 6.38, and then adding a very small amount of stronger base to effect complete neutralization of the remainder of the sulfonic acid.

25 Claims, 1 Drawing Figure

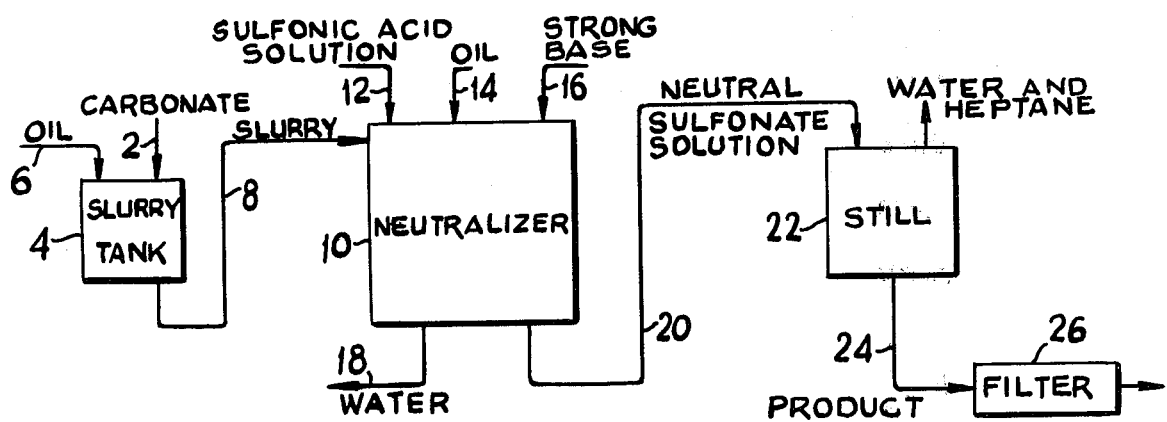

PROCESS FOR PRODUCING METAL SALTS OF OIL-SOLUBLE ORGANOSULFONIC ACIDS

CROSS-REFERENCE TO RELATED APPLICATION

This application is a continuation-in-part of copending application Ser. No. 539,595, filed Jan. 8, 1975, now abandoned. This invention relates to an improved method for producing neutral metal salts of organosulfonic acids.

BACKGROUND OF THE INVENTION

Salts of high molecular weight sulfonic acids of organic compounds have found use as rust inhibitors in motor fuels and lubricating oils, and as rubber plasticizers. See, for example, R. G. King and G. W. Thielcke, U.S. Pat. No. 2,764,548, which is incorporated herein by reference. Other uses for such salts are found in textile treating solutions, and as wetting agents.

The most important salts commercially are derived from mono-, di- and trisulfonic acids of aliphatic and aromatic hydrocarbons, containing from about 6 to about 60 carbon atoms, including branched and straight chain alkanes, mono- and poly- cyclic aromatics and alkyl substituted such compounds. The molecular weights will range from about 150 to about 1500. Monosulfonic acids with molecular weights greater than about 350 tend to be oil soluble while those with lower molecular weights tend to be water soluble. In the case of di- and tri-sulfonic acids, the minimum molecular weights for oil solubility tend to be higher. Particularly valuable salts are alkali metal, alkaline earth metal, lead and zinc salts of such organosulfonic acids as dinonylnaphthalene mono- and disulfonic acid. Special mention is made of such salts, and especially the sodium, potassium, lithium, calcium, magnesium, barium and zinc salts of dinonylnaphthalene disulfonic acid. The latter family of salts are disclosed in the said patent, U.S. Pat No. 2,764,548. The barium, calcium and lithium salts, particularly, form products having exceptional rust inhibiting properties.

Commercially, such salts are often prepared by using oxides or hydroxides of the corresponding metal to neutralize the sulfonic acid. However, this is disadvantageous because the oxides and hydroxides are highly caustic and, in some cases, toxic. Moreover, end-point control is difficult and requires accurately stopping the flow of neutralizing agent. Exact neutrality can be very important because, for example, overneutralized metal salt sulfonates tend to be difficult to filter. Also, the salts of sulfonic acids are frequently used in combination with ester lubricants or other additives including amines and weak acids which cannot tolerate free acidity or basicity.

In the said patent, U.S. Pat. No. 2,764,548, it is suggested that the metal be reacted in the form of a carbonate with the organosulfonic acid, and this indeed is more economical, much safer, and more controllable. However, even with the carbonate, as is specifically taught in the patent, end-point control is very important from a processing standpoint, because if an excess of carbonate is added, filtration is necessary to free the finished product from turbidity. Thus, it is taught that the batch should be transferred to solvent recovery when the neutrality point has been reached.

Mackinnon, U.S. Pat. No. 2,702,280, describes the preparation of sulfonic acid salt detergents by the neutralization of the corresponding benzenesulfonic acid with carbonates, then with an alkali metal hydroxide in two steps. It is said to be essential to carry out the reaction only to 70 to 85% completion with carbonate and then to go the rest of the way with the hydroxide, 15 to 30% of the neutralization being achieved with the hydroxide — a very substantial amount.

Jacob et al, U.S. Pat. No. 2,688,035, also deal with neutralizing sulfonic acid with alkali carbonates, but use a small excess of the latter, and leave it in the reaction product — to prevent formation of free acid. Jacob et al furthermore, before making any adjustments with acid, homogenize the mixture containing the excess carbonate and measure the pH on a sample in which carbonate is homogeneously dispersed therethrough.

It has now been discovered that, in such systems, carbonate neutralization appears to be limited by a carbonate (bicarbonate)/acid equilibrium, which prevents complete neutralization of the sulfonic acid present. As will be understod by those skilled in this art, the term "carbonate/acid equilibrium," as used herein, means also "bicarbonate/acid equilibrium," because the ultimate working equilibrium includes the bicarbonate ion. This discovery was not foreshadowed by the prior art because King et al call for neutralization precisely with carbonate only; Mackinnon doesn't use enough carbonate to reach any equilibrium point; and Jacob et al use a system with excess carbonate and measure the pH on carbonate-containing samples — which obscures the presence of an equilibrium. In applicants' work, measurements on carbonate-free samples have determined that the equilibrium point is just shy of a true end point, regardless of the excess of carbonate present. As a result of this unexpected observation, which could not have been made by King et al, Mackinnon, or Jacob et al, the subsequent finding that the addition of a very tiny amount of strong base pushes the neutralization to completion, and gives a substantial improvement in process economics and in the quality of the product, is most surprising. These process advantages have wide applicability to the formation of numerous metal salts of organosulfonic acids. Surprisingly, it is critical to add the strong base after the carbonate. If the order is reversed, all advantages are lost. Moreover, if water is excluded from the process, no neutralization occurs with metal carbonates. The key requirement in selection of the strong base is to use one which has a base strength sufficiently greater than that of the bicarbonate ion to effect complete neutralization. The pKa of the conjugate acid ($H_2CO_3$) of the bicarbonate ion ($HCO_3-$) is 6.38. Accordingly, suitable strong bases will be those whose conjugate acid have pKa's of greater than 7.

In the systems of the present invention, the relevant equilibrium would be given by $CO_2 + H_2O \rightleftharpoons H^+ + HCO_3-$, and the equilibrium constant is:

$$K = \frac{[H^+][HCO_3^-]}{[CO_2]}$$

Taking the expression further, $$\log K = \log H^+ + \log \frac{[HCO_3^-]}{[CO_2]}$$

and

-continued $$pH - pK = \log \frac{[HCO_3^-]}{[CO_2]}$$

Because the known value of pK for this equilibrium is 6.38, it follows that for $(HCO_3-) = (CO_2)$, the equilibrium pH will equal the pK or 6.38. Thus, the relative concentrations of $HCO_3-$ and $CO_2$ are important. since the solubilities of bicarbonates tend to be greater in acid media while that of $CO_2$ is greater in basic media, the pH at equilibrium is very close to pK.

SUMMARY OF THE INVENTION

According to the present invention, metal salts of organosulfonic acids are produced by
(i) providing a mixture comprising the organosulfonic acid and a small, effective amount of water;
(ii) adding to the mixture a compound of at least one alkali metal salt, alkaline earth metal salt, lead or zinc in the form of a carbonate, in an amount sufficient to provide a molar excess of the compound of at least about 1%;
(iii) reacting the mixture until the carbonate/acid equilibrium point is reached; and
(iv) adding a small amount of a compound which has a base strength greater than that of bicarbonate ion, sufficient to effect complete neutralization of the sulfonic acid.

When used herein and in the appended claims, the term "small, effective amount of water" in step (i) means at least 2 moles of water per equivalent of the sulfonic acid.

The term "until the carbonate/acid equilibrium point is reached" in step (iii) means that point in time in the reaction cycle where the hydrogen ion concentration measured on a substantially carbonate-free sample of the reaction mixture becomes stabilized at a fixed value. Conveniently, and preferably, the equilibrium point is determined by following the pH of a carbonate-free sample or samples. It will always become fixed at a value in the range of from about 6.0 to about 6.38 (carbonate-free basis). When used herein, "carbonate-free" also means "bicarbonate free."

The term "small amount of a metal compound" in step (iv) means up to about 1% by weight, based on the weight of the carbonate.

BRIEF DESCRIPTION OF THE DRAWING

The drawing illustrates in flow diagram form, an arrangement of processing components in which the present process may be practiced.

DETAILED DESCRIPTION OF THE INVENTION.

Referring to the drawing, metal carbonate is introduced through conduit 2 into slurry tank 4 and mixed with an inert suspending medium, e.g., a hydrocarbon oil, which is introduced through conduit 6. The slurry thus produced is transferred through conduit 8 and is slowly introduced into neutralizer 10, which contains sulfonic acid solution, e.g., in an inert solvent, such as naphtha or heptane and water, e.g., 5-20% by weight, and optionally, a hydrocarbon oil added through respective conduits 12 and 14. In neutralizer 10, the metal sulfonate is produced and carbon dioxide gas is liberated. If desired, the mixture can be agitated and heated, e.g., to 60°-90° C. to speed attainment of the carbonate/acid equilibrium point. Then a relatively small amount, e.g., less than 1% by weight of the carbonate previously added, of strong metal base is introduced through port 16 into the reaction mixture in neutralizer 10. Neutralization, as measured by conventional titrations, is substantially complete in only a very short time. At this point, a precisely neutral salt has been formed and the solution can be used as such, or worked up by a conventional technique.

In one work up procedure, the water and volatile solvent are stripped by distillation and the oil soluble salt remains dissolved in the hydrocarbon oil still bottoms; this can be filtered and, if the hydrocarbon oil content is adjusted to provide from 30 to 70% of metal sulfonate, a valuable commercial concentrate is provided directly.

If, for example, the mixture in neutralizer 10 is allowed to settle after the strong base addition is complete, water can be separated and drawn off, e.g., through conduit 18. Then the neutral organic layer is transferred through conduit 20 to still 22, wherein the volatile inert organic solvent and water are removed overhead and finally the solution of product in hydrocarbon oil is transferred through conduit 24 to filter 26, from which it is taken for packaging and storage.

Obviously, suitable modifications will be used if the starting organosulfonic acid is water soluble. These are conventional and well within the capabilities of those skilled in this art. The most important distinction will be in the work up procedure, in which any water layer, which may contain the product, is not drawn off and discarded, but rather is treated by distilation, thin film evaporation, liquid-liquid extraction or other techniques if the solvent (water)-free product is desired.

Although the process conditions can vary over rather broad ranges, best results with oil-soluble organosulfonic acids appear to result from use of a general procedure outlined as follows:

A quantity of organosulfonic acid, e.g., 20-50% of dinonylnaphthalene sulfonic acid, dissolved in 35-55% of a volatile solvent, such as naphtha or heptane, and 1-25 and preferably, 10-20%, water (all parts by weight) is introduced into the reactor and heated to 50°-65° C. Then a slurry in oil, e.g., mineral oil, of the respective alkali metal carbonate, alkaline earth metal carbonate, lead carbonate or zinc carbonate in an amount sufficient to provide from 1 to 10 and preferably, from 2 to 4 mole % excess of the latter per mole of sulfonic acid groups is added over a long enough period to accommodate any foaming during reaction to produce the metal sulfonate and carbon dioxide gas. To assist reaching equilibrium, the mixture can be refluxed, e.g., at 75°-80° C. and stirred and samples are taken and titrated, or check with Congo red indicator paper or the like until reaction is as complete as possible as indicated by taking samples, allowing the carbonate to settle, centrifuging, filtering, etc., and then measuring hydrogen ion concentration. The stabilization of hydrogen ion content, i.e., the attainment of equilibrium, may take 3 to 4 hours. At this point, there is added a small amount of a strong base, which can include the metal used in the carbonate or a different one, but preferably the former, and illustratively is a metal hydroxide, metal oxide or even a quaternary ammonium base, and the like, but preferably, the oxide or hydroxide. Generally, only from about 0.1 to 1% by weight (based on the original weight of carbonate) is used and again the end point is determined by titration tests for acid or base numbers, respectively, in accordance with well known techniques. A clear haze-free neutral solution is produced which can be used as such. However, it is also convenient to cool the mixture, e.g., to 65°–70° C. and allow it to settle. After the excess carbonate settles, a clear, neutral sulfonate-in-oil solution is produced which can be used as such. A lower water layer may also be present, depending on the amount of water in the original mixture. Neutralization produces water and simultaneously reduces the solubility of water in the system.

DESCRIPTION OF THE PREFERRED EMBODIMENTS

The following examples illustrate the method of the present invention. They are not intended to limit the scope of the claims in any manner whatsoever. All percentages are by weight, except where otherwise indicated.

EXAMPLE 1

Nine thousand seventy one pounds of a solution of approximately 35.5% dinonylnaphthalene sulfonic acid, 45% heptane, 15% water and 5% unsulfonated nonylnaphthalenes, produced by the process described in U.S. Pat. No. 2,765,548, is added to a steam-jacketed 1600 gallon reactor at 50° C. A slurry of 759 lbs. of barium carbonate (7.5% molar excess based on the sulfonic acid) in about 200 gallons of mineral oil diluent is prepared in a separate vessel. The slurry is added to the acid mixture with strong agitation over a period of 1.5 hours. Carbon dioxide is evolved with foaming and heptane vapor is condensed and returned to the reactor-neutralizer. Then 100 gallons more of mineral oil is added. The mixture is heated to refluxing at 78° C. and refluxed for 3 hours with agitation to produce an equilibrium with the carbonate. After settling the excess carbonate, the pH of a carbonate-free sample (1:10 wt./wt. in 50–50 mixture of heptane (88% isopropanol-12% water)) is 6.17. The acid number is 0.03. Then ½ pound of calcium hydroxide is added as the strong base to the mixture at about 71° C. and the mixture is agitated without supplying more heat for about 1 hour. A 10 g. sample, diluted as above, has a pH of 7.5. The base number is 0.03 (ml. of 0.1N HCl per 1 g. of sample). The mixture is cooled to 65°–70° C., allowed to settle and the lower water layer is drawn off. The remaining water and heptane are removed by distillation under vacuum to 138° C. and the product is filtered to remove unreacted carbonate. There is produced a clear, neutral solution of the barium salt of dinonylnaphthalene sulfonic acid in mineral oil.

The procedure is repeated on a smaller scale with a 2 and a 4% molar excess of barium carbonate, respectively, and using barium octahydrate as the strong base. Substantially the same results are obtained.

EXAMPLE 2

Two hundred grams of dinonylnaphthalene sulfonic acid solution of the composition used in Example 1 is placed in a 1000 ml. flask fitted with a stirrer, thermometer and condenser. The flask is heated and 8.55 g. of powdered calcium carbonate (10% excess based on the sulfonic acid) is added with agitation. After a few minutes, carbon dioxide evolution ceases. The mixture is refluxed for 30 minutes, then the solids are allowed to settle. A 10 ml. sample diluted with a mixture of heptane and isopropanol as described in Example 1, and then filtered to remove the excess carbonate, has a pH of about 6.0, indicating that the carbonate/acid equilibrium has been reached. Then 2.0 g. of calcium hydroxide in 98 g. of mineral oil is prepared and 2 mls. of the mixture is added (0.02 g. of strong base). Finally, 60 g. of mineral oil is added, and the heptane and water are distilled off. The remaining fluid is filtered hot, at 130°–140° C., through a pressure filter. There is produced a completely neutral solution of calcium dinonylnaphthalene sulfonate in mineral oil.

The following demonstrates the need for a small, effective amount of water in the reaction between metal carbonate and sulfonic acids.

100 grams of a solution of dinonylnaphthalene sulfonic acid in mineral oil, containing 34.4% acid and 1.2% water by weight, are placed in a 500 ml. flask. Five grams of powdered calcium carbonate, USP grade, is added and dispersed by vigorously swirling the contents of the flask. No foaming occurs, indicating that the carbonate and acid are not reacting. Then 3 milliliters of water are added individually and mixed after each addition. There is no evidence of reaction. Finally, after a fourth milliliter of water is added to the contents of the flask and mixed, vigorous foaming begins, accompanied by gradual disappearance of most of the calcium carbonate.

This demonstrates that at least a small amount of water is necessary for the reaction of calcium carbonate and sulfonic acid, and further, that a definite minimum quantity of water is required. In this case, the minimum requirement corresponds to 3 or more moles of water per equivalent of sulfonic acid. This suggests that water present as water of hydration is not effective, and that un-bound water is required.

EXAMPLE 3

The procedure of Example 2 is repeated, modified to the extent that 0.02 g. of calcium hydroxide is added as the free base and 158 g. of di-(2-ethylhexyl)azelate is substituted for the mineral oil and is added to the neutral solution before the heptane and water are distilled off. Di-(2-ethylhexyl)-azelate is a synthetic ester having a boiling point of 376° C. (760 mm.). There is obtained a completely neutral solution of calcium dinonylnaphthalene sulfonate in di-(2-ethylhexyl)azelate, which is suitable for use in lubricants for turbines, e.g., in aircraft engines.

Obviously, other variations will suggest themselves to those skilled in this art in view of the above detailed description. For example, instead of dinonylnaphthalene sulfonic acid, other organosulfonic acids can be used such as hexane sulfonic acid, hexadecane sulfonic acid, the sulfonic acid derivative of white mineral oil, dinonylnaphthalene disulfonic acid, dodecyl benzene sulfonic acid, polydodecyl benzene sulfonic acids, didodecylnahthalene sulfonic acid, petroleum sulfonic acids, and the like. Instead of barium carbonate and calcium carbonate, sodium carbonate, potassium carbonate, lithium carbonate, magnesium carbonate, lead carbonate and zinc carbonate can be used. Instead of barium hydroxide and calcium hydroxide, sodium hydroxide, potassium hydroxide, lithium hydroxide, magnesium oxide, lead oxide and zinc oxide can be used. When neutralizing oil soluble sulfonic acids, obviously instead of heptane as an inert volatile organic solvent, naphtha, toluene and chloroform can be used. Furthermore, the use of a hydrocarbon oil can be omitted, or it can be added at any stage of the process. The amount of oil can be varied, but usually from 40 to 70% by weight of metal sulfonate in the final composition is preferred. Furthermore, diisooctyl sebacate and di-(2-ethylhexyl)adipate, can be substituted for di-(2-ethylhexyl)azelate before removing the inert solvent and water to thereby produce a solution of the metal salt in these ester lubricants. Obviously, although batch processes have been described, the process can be practiced in a continuous fashion. Instead of adding the metal carbonate as a slurry, it can be added in other forms, such as powder, if, for example, an appropriate vapor lock is used. All such obvious modifications are within the full intended scope of the appended claims. We claim:

1. A process for producing a metal salt of an organosulfonic acid and a metal selected from alkali metals, and alkaline earth metals, said process comprising the steps of:
   (i) providing a mixture comprising the organosulfonic acid and at least 2 moles of water per equivalent of said sulfonic acid;
   (ii) adding to the mixture a compound of at least one of said metals in the form of a carbonate, in an amount sufficient to provide a molar excess of said compound of at least about 1%;
   (iii) reacting and heating the mixture until the carbonate/acid equilibrium point is reached; and
   (iv) adding a small amount of up to about 1%, based on the weight of the carbonate, of a compound selected from a metal oxide or metal hydroxide which has a base strength greater than that of bicarbonate ion, sufficient to effect complete neutralization of the remainder of said organosulfonic acid.

2. A process as defined in claim 1 wherein the equilibrium point is taken as the point in time where the hydrogen ion concentration measured on a substantially carbonate- and bicarbonate-free sample of the reaction mixture becomes stabilized at a fixed value.

3. A process as defined in claim 2 wherein the end point is taken as the point in time where the pH of the substantially carbonate- and bicarbonate-free sample stabilizes in a range of from about 6.0 to about 6.38.

4. A process as defined in claim 1 wherein the organosulfonic acid is an oil-soluble organosulfonic acid, and said mixture also includes an inert solvent.

5. A process as defined in claim 1 wherein the compound added in step (iv) is a metal oxide or a metal hydroxide.

6. A process as defined in claim 5 wherein the compound added in step (iv) is the same as the metal of the carbonate added in step (ii).

7. A process as defined in claim 4 wherein the oil-soluble organosulfonic acid is selected from mono-, di- and trisulfonic acids of aliphatic or aromatic hydrocarbons, and has a molecular weight of greater than about 350.

8. A process as defined in claim 7 wherein the oil-soluble organosulfonic acid dinonylnaphthalene sulfonic acid.

9. A process as defined in claim 1 wherein the organosulfonic acid is dinonylnaphthalene disulfonic acid.

10. A process as defined in claim 1 wherein the metal in the carbonate used in step (ii) is selected from sodium, potassium, lithium, barium, calcium, and magnesium.

11. A process as defined in claim 10 wherein the metal in the carbonate used in step (ii) is barium.

12. A process as defined in claim 10 wherein the metal in the carbonate used in step (ii) is calcium.

13. A process as defined in claim 10 wherein the metal in the carbonate used in step (ii) is lithium.

14. A method as defined in claim 5 wherein the metal compound added in step (iv) is barium hydroxide.

15. A method as defined in claim 5 wherein the metal compound added in step (iv) is calcium hydroxide.

16. A method as defined in claim 5 wherein the metal compound added in step (iv) is lithium hydroxide.

17. A process for producing a metal salt of dinonylnaphthalene sulfonic acid and a metal selected from sodium, potassium, lithium, calcium, magnesium, and barium, said process comprising the steps of:
   (i) forming a solution of dinonylnaphthalene sulfonic acid in an inert volatile organic solvent and at least two moles of water per equivalent of said sulfonic acid;
   (ii) adding to the solution a compound of at least one of said metals in the form of a carbonate, in an amount sufficient to provide a molar excess of said compound in the range of from 1 to 10%;
   (iii) reacting and heating the mixture at a temperature of at least about 60° C. until the carbonate/acid equilibrium point is reached and the pH measured on a substantially carbonate- and bicarbonate-free sample would fall in the range of from about 6.0 to about 6.38; and
   (iv) adding a small amount of up to 1%, based on the weight of the carbonate, of a metal compound which has a base strength greater than that of the bicarbonate ion, sufficient to effect complete neutralization of the remainder of said dinonylnaphthalene sulfonic acid.

18. A process as defined in claim 17 including the steps of adding a relatively non-volatile hydrocarbon oil to the reaction mixture at any stage, and as a final step, selectively removing the inert volatile organic solvent and water, to produce a solution of the metal salt of said sulfonic acid in said hydrocarbon oil.

19. A process as defined in claim 18 wherein the volatile solvent and water are removed by distillation and the amount of hydrocarbon oil used produces a solution comprising 40 to 60% by weight of the metal sulfonate.

20. A process as defined in claim 17 wherein the metal in the carbonate compound used in step (ii) and in the metal compound of step (iv) is barium.

21. A process as defined in claim 17 wherein the metal in the carbonate compound used in step (ii) and in the metal compound of step (iv) is calcium.

22. A process as defined in claim 17 wherein the metal in the carbonate compound used in step (ii) and in the metal compound of step (iv) is lithium.

23. A process as defined in claim 17 including the steps of adding a relatively non-volatile ester lubricant to the neutral mixture, selectively removing the inert volatile organic solvent and water and thereby producing a solution of the metal salt of said sulfonic acid in said ester lubricant.

24. A process as defined in claim 1 wherein said heating in step (iii) is carried out in the range of from about 60° C. to about 90° C.

25. A process as defined in claim 1 wherein said heating in step (iii) is carried out at a temperature of from about 75° C. to about 80° C.

* * * * *